United States Patent [19]

Juneja

[11] Patent Number: 4,824,602

[45] Date of Patent: Apr. 25, 1989

[54] PROCESSES FOR PURIFICATION OF QUATERNARY CATIONIC SURFACTANT MATERIALS AND COSMETIC COMPOSITIONS CONTAINING SAME

[75] Inventor: Prem S. Juneja, Cincinnati, Ohio

[73] Assignee: The Procter & Gamble Company, Cincinnati, Ohio

[21] Appl. No.: 136,591

[22] Filed: Dec. 22, 1987

Related U.S. Application Data

[63] Continuation of Ser. No. 923,372, Oct. 27, 1986, abandoned.

[51] Int. Cl.$^4$ .................. A61K 7/075; C07C 85/26; C11D 1/65; C11D 3/37
[52] U.S. Cl. ................... 252/547; 252/89.1; 252/153; 252/174.15; 252/548; 252/550; 252/551; 252/DIG. 5; 252/DIG. 13; 424/70; 564/292
[58] Field of Search ............ 424/70; 252/153, 174.15, 252/547, DIG. 13; 564/292

[56] References Cited

U.S. PATENT DOCUMENTS

| | | | |
|---|---|---|---|
| 4,016,209 | 4/1977 | Wagner | 564/295 |
| 4,217,429 | 8/1980 | Wagner | 564/292 |
| 4,387,090 | 6/1983 | Bolich | 424/70 |
| 4,423,032 | 12/1983 | Abe | 424/70 |
| 4,452,732 | 6/1984 | Bolich | 252/547 |
| 4,472,375 | 9/1984 | Bolich | 424/70 |
| 4,636,329 | 1/1987 | Steuri | 252/106 |
| 4,638,089 | 1/1987 | Hisamoto | 564/292 |
| 4,658,839 | 4/1987 | Dallal | 132/7 |

FOREIGN PATENT DOCUMENTS 2157168A 10/1985 United Kingdom ........... 252/174.15

*Primary Examiner*—Dennis Albrecht
*Attorney, Agent, or Firm*—Douglas C. Mohl; Steven J. Goldstein; Richard C. Witte

[57] ABSTRACT

The present invention relates to processes for purifying quaternary cationic surfactant materials and rendering said materials substantially free of ultraviolet absorbing impurities having a maximum absorption in the range of from about 260 nm to about 280 nm. This invention also relates compositions containing purified quaternary cationic surfactant materials.

7 Claims, No Drawings

PROCESSES FOR PURIFICATION OF QUATERNARY CATIONIC SURFACTANT MATERIALS AND COSMETIC COMPOSITIONS CONTAINING SAME

This is a continuation of application Ser. No. 923,372, filed on Oct. 27, 1986, now abandoned.

TECHNICAL FIELD

This invention relates to processes for purifying quaternary cationic surfactant materials and compositions containing the purified cationic surfactant materials.

BACKGROUND OF THE INVENTION

Quaternary cationic surfactant materials are widely known for use in softening, cleaning and cosmetic compositions.

Many hair care compositions, especially conditioning products, contain long chain quaternary ammonium compounds. Compositions are disclosed in U.S. Pat. No. 3,155,591, Hilfer, issued Nov. 3, 1964, in U.S. Pat. No. 4,269,824, Villamarin et al., issued May 26, 1981. Hair care compositions have also been disclosed which contain quaternary ammonium salts and silicone materials in U.K. patent application No. 2,066,659, Abe, published July 15, 1981, all of which are incorporated herein by reference.

Although widely used, all of the problems of making compositions containing such cationic surfactant materials have not been solved.

It has been found that frequently commercial supplies of certain quaternary cationic surfactant materials contain levels of a UV absorbing impurity which has a maximum absorption at from about 260 nm to about 280 nm; the amount of which impurity varies by lot of material. Surprisingly, this has been found to adversely impact the viscosity and stability of certain compositions made therewith. The impure materials vary in color from off-white to brown; they vary in physical condition from partially dry sticky powders to pasty solids. The variation in level also renders measurement less accurate.

Applicant has now discovered that compositions made with quaternary cationic surfactant materials purified by a process described herein, yield significantly improved viscosity properties to certain hair care compositions made therewith.

It is therefore an object of the present invention to provide a process for purifying quaternary cationic surfactant materials.

It is a further object of the invention to provide stable compositions with controlled viscosity containing quaternary cationic surfactant materials.

It is a further object of the invention to provide purified quaternary cationic surfactant materials for use in such compositions.

It is a further object to provide purified quaternary cationic surfactant materials in the form of free-flowing powders.

These and other objects will be made clear from the description herein.

All percentages and ratios herein are by weight unless otherwise noted.

SUMMARY OF THE INVENTION

The present invention provides hair care compositions comprising purified quaternary cationic surfactant materials of the general formula

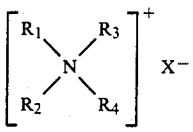

wherein $R_1$ and $R_2$ are aliphatic groups containing from about 12 to about 22 carbon atoms, $R_3$ and $R_4$ are hydrogen or short chain alkyl groups containing from about 1 to about 4 carbon atoms and X is an ion selected from halogen, acetate, phosphate, nitrate and alkyl sulfate radicals. The present invention also provides a purification process comprising washing with about 2.0 milliliters of an organic solvent per gram of quaternary cationic surfactant material. Acetonitrile is a highly preferred solvent herein; where acetonitrile is used, at least about 0.5 ml/gm is required.

DETAILED DESCRIPTION OF THE INVENTION

Quaternary Cationic Surfactant Materials

Compositions of the invention comprise one or more purified quaternary cationic surfactant materials. Such surfactant materials contain quaternary ammonium hydrophilic moieties which are positively charged when dissolved in the aqueous compositions of the present invention. Quaternary cationic surfactant materials are those described in the following publications, all of which are incorporated herein by reference: McCutcheon's, Detergents & Emulsifiers (North American Ed. 1979); Schwartz et al., Surface Active Agents, Their Chemistry and Technology, New York; Interscience Publishers, 1949; U.S. Pat. No. 3,155,591, Hilfer, issued Nov. 3, 1964; U.S. Pat. No. 3,929,678, Laughlin, issued May 25, 1976, and U.S. Pat. No. 4,387,090, Bolich, Jr., issued June 7, 1983.

The quaternary ammonium-containing cationic surfactant materials useful herein are those of the general formula:

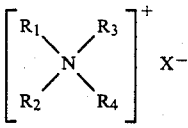

wherein $R_1$ and $R_2$ are aliphatic groups having from about 12 to about 22 carbon atoms; $R_3$ and $R_4$ are hydrogen or alkyl chains containing from about 1 to about 4 carbon atoms and X is an ion selected from halogen, acetate, phosphate, nitrate and alkyl sulfate radicals.

Preferred quaternary ammonium salts include dialkyl dimethyl ammonium chlorides, wherein the alkyl groups have from about 12 to about 22 carbon atoms and are derived from long chain fatty acids such as hydrogenated tallow fatty acids. Examples of such compounds include ditallow dimethyl ammonium chloride, ditallow dimethyl ammonium methyl sulfate, di(hydrogenated tallow) dimethyl ammonium chloride, dihexadecyl dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, and di(coconut alkyl) dimethyl ammonium chloride. Ditallow dimethyl ammonium chloride, dicetyl dimethyl ammonium chloride, and di(hydrogenated tallow) dimethyl ammonium chloride are preferred. Di(hydrogenated tallow) dimethyl ammonium chloride is particularly preferred.

The quaternary cationic surfactant materials described above are available in the impure form as products of commerce e.g., from Sherex under the trademark Adogen ® and from Akzo under the trademark Arquad ®. Use of the impure materials in certain hair care compositions surprisingly results in a lowered viscosity for compositions having a viscosity of 10,000 cps or more. The actual viscosity of the composition made with the impure materials varies with the level of impurity found in the lot of material used.

The purified quaternary cationic surfactant materials useful in compositions of the invention are substantially free of impurities which show a strong UV absorption property with maximum absorption at a wavelength of from about 260 nm to about 280 nm. more preferably from about 270 nm to about 275 nm. "Substantially free" as used herein means that the purified materials have an absorption of less than about 0.25 absorption units full scale (aufs). This will be described in detail, infra.

The purified quaternary cationic surfactant materials also are free-flowing powders. The unpurified materials may contain water and/or other solvents and impurities causing a pasty, wet consistency. The purification process of the invention removes such solvents and impurities resulting in a dry free-flowing powder which is easier to measure accurately and to process.

Hair Care Compositions

The hair care compositions of the invention are stable compositions, which may be in the form of shampoos, conditioning shampoos, hair conditioners, or rinses.

Hair care compositions of the invention comprise from about 0.05% to about 10% of a purified quaternary cationic surfactant material.

Preferred hair care compositions of the invention further comprise a silicone conditioning agent which impart conditioning benefits to human hair when applied in the present compositions. (As used herein, the term "silicone conditioning agent" refers to such silicone conditioning materials, singly or in combination.) Non-volatile silicones are preferred.

Preferred silicone conditioning agents include the polydimethylsiloxanes, more preferably, the linear polydimethylsiloxanes of the general formula:

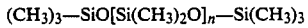

$(CH_3)_3-SiO[Si(CH_3)_2O]_n-Si(CH_3)_3$ wherein n is from 1 to 15,000, preferably from 20 to 7000. Preferred polydimethylsiloxanes are unsubstituted or are vinyl, phenyl, carboxy, alkoxy, mercapto, alkyl, or amino substituted. Particularly preferred silicone conditioning agents include the unsubstituted and the amino or alkoxy substituted linear polydimethylsiloxanes, and mixtures thereof.

Examples of silicone oils useful in the present invention include Dow Corning 200 Fluid and Dow Corning Q2-8075 Aminofunctional Fluid (manufactured by the Dow Corning Corporation); Silicone Copolymer F-755 (manufactured by SWS Silicones Corp.), and SE 76 Silicone Gum (manufactured by General Electric). Polydimethylsiloxane conditioning agents are also disclosed in the following documents, all incorporated by reference herein: U.S. Pat. No. 4,387,097, Bolich, Jr., issued June 7, 1983; British Specification No. 2,066,659, Abe, published July 15, 1981; Wendel, et al, "Organofunctional Silicones for Personal Care Applications", 98 *Cosmetics & Toiletries* 103–106 (1983); and Todd, et al., "Volatile Silicone Fluids for Cosmetics", 91 *Cosmetics & Toiletries* 27–32 (1976).

One preferred composition is a shampoo comprising from about 0.1% to about 10% of a purified quaternary cationic surfactant material, from about 0.5% to about 50% of a synthetic anionic surfactant, and water.

Useful surfactants for compositions of the invention are described in the following documents, all incorporated by reference herein: M. C. Publishing Co., *McCutcheon's Detergents & Emulsifiers*, (North American edition, 1979); Schwartz, et al., *Surface Active Agents, Their Chemistry and Technology* (1949); and U.S. Pat. No. 3,929,678, Laughlin et al., issued Dec. 30, 1975.

Preferred surfactants in shampoo compositions of the invention include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, X is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl trioxyethylene sulfate; lithium tallow alkyl trioxyethylene sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight $C_{12-13}$ compounds; from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Examples of other anionic synthetic detergents which come within the terms of the present invention are the reaction product of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic detergents of this variety are set forth in U.S. Pat. Nos. 2,486,921; 2,486,922; and 2,396,278.

Still other anionic synthetic detergents include the class designated as succinamates. This class includes such surface active agents as disodium N-octadecylsulfosuccinamate; tetrasodium N-(1,2-dicarboxyethyl)-N-octadecylsulfo-succinamate; diamyl ester of sodium sulfosuccinic acid: dihexyl ester of sodium sulfosuccinic acid; dioctyl esters of sodium sulfosuccinic acid.

Other suitable anionic detergents utilized herein are olefin sulfonates having about 12 to about 24 carbon atoms. The term "olefin sulfonates" is used herein to mean compounds which can be produced by the sulfonation of α-olefin by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-cicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 of Phillip F. Pflaumer and Adrian Kessler, issued July 25, 1967, titled "Detergent Composition", the disclosure of which is incorporated herein by reference.

Another class of anionic organic detergents are the -alkyloxy alkane sulfonates. These compounds having the following formula:

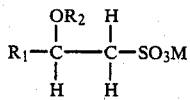

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein to provide superior cleaning levels under household washing conditions include: potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecylsulfonate, and ammonium-n-propoxydodecylsulfonate.

Another suitable class of anionic surfactants are the water-soluble salt of organic, sulfuric acid reaction products of the general formula:

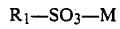

wherein $R_1$ is chosen from the group consisting of a straight or branched chain, saturated aliphatic hydrocarbon radical having from 8 to 24, preferably 12 to 18 carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 28 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Nonionic surfactants may also be present. Such surfactants are most commonly produced by the condensation of an alkylene oxide (hydrophilic in nature) with an organic hydrophobic compound, which is usually aliphatic or alkyl aromatic in nature. The length of the hydrophilic or poly-alkylene moiety which is condensed with any particular hydrophobic compound can be readily adjusted to yield a water-soluble compound having the desired degree of balance between hydrophilic and hydrophobic elements. Such nonionic surfactants include polyethylene oxide condensates of alkyl phenols, condensation products of aliphatic alcohols with ethylene oxide, condensation products of ethylene oxide with a hydrophobic base formed by condensation of propylene oxide with propylene glycol and condensation products of ethylene oxide with the product resulting from the reaction of propylene oxide and achieve diamine. Another variety of nonionic surfactant is the non-polar nonionic, typified by the amine oxide surfactants. Preferred nonionic surfactants include ceteareth-20, steareth-20 and ceteth-2.

Other useful optional surfactants include zwitterionic surfactants and amphoteric surfactants.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

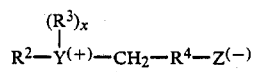

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphate, and phosphate groups.

Examples include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, lauryl bis-(2-hydroxypropyl)alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl)sulfopropyl betaine and the like; amido betaines and amidosulfobetaines, wherein the RCONH(CH$_2$)$_3$ radical is attached to the nitrogen atom of the betaine are also useful in this invention. The amido betaines are preferred for use in some of the compositions of this invention. A particularly preferred composition utilizes an amido betaine, a quaternary compound, a silicone, a suspending agent and has a pH of from about 2 to about 4.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g. carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

A desirable component of the silicone containing shampoo compositions of the present invention is a suspending agent. Two preferred materials are xanthan gum and long chain acyl derivatives as well as other long chain materials.

Xanthan gum is an agent which can be used in the present compositions to suspend the silicone fluid. This biosynthetic gum material is commercially available and is a heteropolysaccharide with a molecular weight of greater than 1 million. It contains D-glucose, D-mannose and D-glucuronate in the molar ratio of 2.8:2.0:2.0. The polysaccharide is partially acetylated with 4.7% acetyl. This information and other is found in Whistler, Roy L. Editor *Industrial Gums—Polysaccharides and Their Derivatives* New York: Academic Press, 1973. Kelco, a Division of Merck & Co., Inc. offers xanthan gum as Keltrol ®. The gum is present at a level of from about 0.4% to about 3%, preferably from about 0.6% to about 1.2% in the compositions of the present invention.

Another suspending agent useful in the present compositions is any of several long chain acyl derivative materials or mixtures of such materials. Included are ethylene glycol esters of fatty acids having from about 16 to about 22 carbon atoms. Preferred are the ethylene glycol stearates, both mono and distearate, but particularly the distearate containing less than about 7% of the monostearate. Other suspending agents found useful are alkanol amides of fatty acids, having from about 16 to about 22 carbon atoms, preferably about 16 to 18 carbon atoms. Preferred alkanol amides are stearic monoethanolamide, stearic diethanolamide, stearic monoisopropanolamide and stearic monoethanolamide stearate.

Still other suitable non-acyl derivative suspending agents are alkyl (C$_{16-22}$) dimethyl amine oxides such as stearyl dimethyl amine oxide.

The suspending agent or mixture of agents is present at a level of from about 0.4% to about 5%, preferably from about 0.5% to about 2.5%. The suspending agent serves to assist in suspending the silicone material and may also give pearlescence to the product.

Another particularly preferred hair care composition herein is a conditioning composition for human or animal hair. Such compositions also comprise from about 0.1% to about 10% of a quaternary cationic surfactant material. The conditioning compositions further comprises from about 0.1% to about 10% of a silicone conditioning agent and from about 0.01% to about 10% of a dimethicone copolyol, and from about 0.1% to about 10% of a lipid vehicle material. Viscosity of the conditioner is at least about 10,000 cps, preferably from about 12,000 cps to about 16,000 cps.

The lipid vehicle materials used in conditioning compounds herein are essentially water insoluble and contain hydrophobic and hydrophilic moieties. Lipid vehicle materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3rd edition, D. Swern, ed. 1979) (incorporated by reference herein). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification No. 1,532,585, published Nov. 15, 1978; and Fukushima, et al., "The Effect of Cetostearyl Alcohol in Cosmetic Emulsions", 98 Cosmetics & Toiletries 89-102 (1983). Fatty esters included among those useful herein are disclosed in U.S. Pat. No. 3,341,465, Kaufman, et al., issued Sept. 12, 1967 also incorporated by reference herein.

Preferred esters for use herein include cetyl palmitate and glycerolmonostearate. Cetyl alcohol and stearyl alcohols are preferred alcohols. A particularly preferred lipid vehicle material is comprised of a mixture of cetyl alcohol and stearyl alcohol containing from abut 55% to about 65% (by weight of mixture) of cetyl alcohol.

The preferred conditioning compositions of the present invention further comprise a silicone containing material (specifically a polyalkylene oxide modified dimethylpolysiloxane, herein referred to as "dimethicone copolyol") which acts as an antiresoiling agent. These dimethicone copolyols reduce deposition of lipid materials and cationic surfactant materials onto the hair. The dimethicone copolyols include those polyalkylene oxide modified dimethylpolysiloxanes of the following formulae:

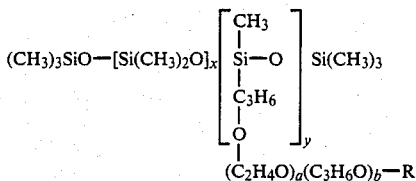

and

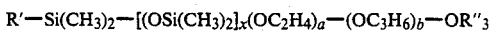

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30.

Dimethicone copolyols among those useful herein are disclosed in the following patent documents, all incorporated by reference herein: U.S. Pat. No. 4,122,029, Gee, et al., issued Oct. 24, 1978; U.S. Pat. No. 4,265,878, Keil, issued May 5, 1981; and U.S. Pat. No. 4,421,769, Dixon, et al., issued Dec. 20, 1983. Such dimethicone copolyol materials are also disclosed, in hair compositions, in British patent application No. 2,066,659, Abe, published July 15, 1981 and Canadian Patent No. 727,588, Kuehns, issued Feb. 8, 1966. Commercially available dimethicone copolyols, useful herein, include Silwet Surface Active Copolymers (manufactured by the Union Carbide Corporation); Dow Corning Silicone Surfactants (manufactured by the Dow Corning Corporation); Silicone Copolymer F-754 (manufactured by SWS Silicones Corp.); and Rhodorsil 70646 Fluid (manufactured by Rhone Poulenc, Inc.), Dow Corning 190 Silicone Surfactant is a preferred dimethicone copolyol.

Optional Materials

The hair care compositions of this invention preferably contain optional components in addition to those already discussed which may modify the physical and performance characteristics of the conditioning product. Such components include salts, buffers, thickeners, solvents, opacifiers, pearlescent aids, preservatives, fragrance, colorants, dyes, pigments, chelators, sunscreens, vitamins, and medicinal agents. Optional components that are among those useful herein are disclosed in U.S. Pat. No. 4,387,090, Bolich, Jr., issued June 7, 1983, incorporated by reference herein.

Salts and buffers may be added to conditioning compositions in order to modify the product rheology. For example, salts such as potassium chloride and sodium chloride, may be added at levels of from about 0.001% to about 1%. Buffers, such as citrate or phosphate buffers, may also be used. Preferably the pH of the present conditioner compositions is from about 3 to about 10, more preferably from about 3 to about 7.

Thickening agents are also preferred optional components useful in hair care compositions herein. Such thickeners include nonionic thickening agents, incorporated at levels from about 0.1% to about 8%. Such agents are polymers which exhibit viscosities exceeding about 200 poises at low shear (about $10^{-2}$ sec$^{-1}$). Included among such polymers are polyoxyethylene, guar gum, methylcellulose, methyl hydroxy propyl cellulose, polypropyl cellulose, polypropyl hydroxy ethyl cellulose, hydroxy ethyl cellulose, starches and starch derivatives, and mixtures thereof.

Purification Process

The quaternary cationic surfactant materials described herein do not, in their pure form, absorb light in the 260-280 nm range of the ultraviolet spectrum. The ultraviolet spectrum includes wavelengths from about 190 nanometers to about 360 nanometers.

The impurity found in the impure materials shows a strong UV absorption property with a maximum absorption at a wavelength of from about 260 to about 280 nm, more specifically, in the range of from 270 nm to 275 nm. Absorption is measured in units called absorption units full scale (aufs). These are standard arbitrary units, which are well known in the art. Impure materials show a wide range in amounts of absorption; the strength of the absorption varying with the amount of impurity present in the material. Use of materials which yield an absorption at from about 260 nm to about 280 nm of 0.25 aufs or higher results in composition with an unacceptable viscosity.

Purified materials show absorption of less than 0.25 aufs, preferably less than 0.20 aufs, more preferably less than 0.15 aufs in the aforementioned range.

Solvent

Acetonitrile is the preferred solvent for use in the purification process. Other solvents such as acetone or diethyl ether may also be used; however, larger amounts of these solvents are required to remove a like amount of impurity from the quaternary cationic surfactant material. Where acetonitrile is the sole solvent, at least about 0.5 mls/gm is required to achieve substantial purification. Below this level inadequate dissolution results in separation difficulties. Preferred processes use at least 5 ml/gm acetonitrile, more preferably 7 mls/gm.

Where other solvents are selected at least about 2 mls/gm is required, preferably at least 10 mls/gm, more preferably at least 15 mls/gm for purification. Mixtures of acetonitrile and another solvent, an intermediate level may be acceptable, varying with the percentage of acetonitrile. Mixtures containing 50% acetonitrile or more are preferred.

Procedure

The quaternary cationic surfactant materials of the invention are rendered substantially free of UV absorbing impurities by the following procedure.

The impure material is stirred with the requisite amount of solvent for from about 60 to about 120 minutes. The mixture is then filtered and washed with additional solvent. Suction is applied to the filtrate for from about 30 to about 60 minutes, during which time a filter cake is formed. The solid is then dried. The absorbance in the UV spectrum is measured by use of a spectrophotometer.

Measurement

To measure the absorbance of a quaternary cationic surfactant material in the aforementioned range, 2.0 gms of the material is stirred with 10 mls. acetonitrile. Any of the UV absorbing impurity present will be dissolved into the acetonitrile. The sample is centrifuged and the UV absorbance of the supernatant is measured.

METHODS OF MANUFACTURE

The process for making compositions of the invention may be any of the conventional means known in the art with the purified cationic surfactant material used in place of impure material. Preferred methods are described in the examples.

EXAMPLE I

Unpurified di(hydrogenated tallow)dimethylammonium chloride (DTDMAC) gave an unacceptable viscosity of 11,000 cp for a conditioning composition comprising from about 0.5% to about 5% of a purified quaternary cationic surfactant material; from about 0.5% to about 5% of a siloxane conditioning compound; from about 5% to about 50% of a synthetic anionic surfactant; from about 0.4% to about 5% of a suspending agent, and water. When tested for UV absorbance there was a strong absorbance with a maximum peak at 273 nm. Absorbance tests yielded 0.615 aufs. Two hundred twenty five grams of this unpurified DTDMAC material was placed in a 4 liter glass beaker. Acetonitrile (1400 ml) was added to the beaker and the mixture vigorously stirred, using a mechanical stirrer, for one hour. This mixture was then filtered on a Buchner funnel. The solid in the funnel was washed with additional 100–200 ml of acetonitrile. Suction was continued until the solid was essentially dry. It was removed from the funnel and spread in a flat glass pan and allowed to air dry for about 24 hours. Yield of the purified material was about 203 grams. The purified DTDMAC was tested for absorbance in the UV spectrum. A small peak remained at 273 nm, now much reduced in size; an absorbance of 0.103 aufs was recorded. This purified Adogen-442 was used to make another batch of the conditioning composition described above. A viscosity of 14,600 was obtained for this product.

EXAMPLE II

A hair conditioner, according to the present invention, was made comprising:

| Component | Weight % |
| --- | --- |
| Dow Corning Q2-8075[1] | 0.50 |
| Dow Corning 190 Silicone Surfactant[2] | 0.50 |
| cetyl alcohol | 1.13 |
| stearyl alcohol | 0.75 |
| purified Adogen 442 - 100P[3] | 1.05 |
| Ceteareth-20[4] | 0.35 |
| glycerol monostearate | 0.25 |
| Lexamine S-13[5] | 0.50 |
| fragrance | 0.25 |
| citric acid | 0.13 |
| preservative | 0.03 |
| distilled water | 94.56 |

[1] trimethylsilylamodimethicone, sold by Dow Corning Corporation
[2] dimethicone copolyol, sold by Dow Corning Corporation
[3] di(hydrogenated tallow) dimethyl ammonium chloride, sold by Sherex Chemical Company, Inc., purified to an absorbance of less than 0.25 aufs.
[4] ethoxylated cetostearyl alcohol
[5] stearamido propyl dimethyl amine, sold by Inolex Corporation All materials, except that preservative and fragrance, were added to distilled water, maintained at a temperature of from 65° C. to 74° C. This mixture was then stirred for 15 minutes. After the solution was cooled to approximately 49° C., the fragrance and preservative were added. The mixture was then cooled to approximately 38° C. and milled under high shear for approximately 2 minutes using a conventional milling apparatus.

Approximately 20 grams of the hair conditioning product thus formed is applied to freshly shampooed and rinsed hair. The composition is then spread over the hair and allowed to stand for approximately 1 minute. Thereafter, the product is rinsed from the hair, leaving the hair with conditioning benefits.

EXAMPLE III

A hair conditioner, according to the present invention, was made comprising:

| Component | Weight % |
| --- | --- |
| dimethicone oil (12,500 cs) | 1.00 |
| Rhodorsil 70646 Fluid[1] | 1.00 |
| cetyl alcohol | 1.50 |
| stearyl alcohol | 1.50 |
| Adogen 442-100P[2] | .75 |
| Lexamine S-13 | 1.00 |
| ceteth-20 | 0.20 |
| fragrance | 0.50 |
| citric acid | 0.20 |
| preservative | 0.03 |
| distilled water | 92.32 |

[1] dimethicone copolyol, sold by Rhone-Poulenc, Inc.
[2] di(hydrogenated tallow) dimethyl ammonium chloride, sold by Sherex Chemical Company, Inc., purified to an absorbance of less than 0.25 aufs.

A hair conditioning product was made, as comprised above, in a manner similar to that described in Example II. This product, when applied to human hair, is useful as a conditioner.

In the above example, stearylamine, diethylaminopropyl stearamide, dimethyl stearamine, tridecylamine, ethyl stearamine, N-tallowpropane diamine, myristylamine, ethoxylated stearylamine, dihydroxyethyl stearylamine and arachidylbehenylamine are substituted, respectively, for the Lexamine S-13 stearamidopropyl dimethylamine, with substantially similar results.

EXAMPLE IV

A hair conditioner, according to the present invention, was made comprising:

| Component | Weight % |
| --- | --- |
| $D_5$ cyclomethicone | 2.00 |
| SE-76 Silicone Gum[1] | 0.15 |
| Silicone Copolymer F-755[2] | 0.50 |

-continued

| Component | Weight % |
|---|---|
| Dow Corning 190 Silicone Surfactant | 0.50 |
| cetyl alcohol | 1.25 |
| stearyl alcohol | 1.25 |
| Adogen 442[3] | 0.75 |
| Lexamine S-13 | 0.75 |
| hydroxyethyl cellulose | 0.50 |
| fragrance | 0.25 |
| citric acid | 0.13 |
| preservative | 0.03 |
| distilled water | 91.94 |

[1]dimethicone gum, sold by General Electric
[2]stearoxy dimethicone, sold by SWS Silicones Corporation
[3]di(hydrogenated tallow) dimethyl ammonium chloride, sold by Sherex Chemical Company, Inc., purified to an absorbance of less than 0.25 aufs.

A conditioning product, as comprised above, is made in a manner similar to that described in Example II. This product, when applied to human hair, is useful as a hair conditioner.

EXAMPLE V

A hair conditioner, according to the present invention, is made comprising:

| Component | Weight % |
|---|---|
| D5 cyclomethicone | 8.00 |
| dimethicone oil | 1.00 |
| Silwet L-720[1] | 2.00 |
| cetyl palmitate | 1.00 |
| glycerol monostearate | 3.00 |
| dicetyl dimethyl ammonium chloride[2] | 2.00 |
| perfume | 0.50 |
| colorant | 0.11 |
| preservative | 0.03 |
| distilled water | 82.36 |

[1]dimethicone coplyol, sold by Union Carbide Corporation.
[2]purified; absorbance in 260 nm–280 nm range of less than 0.25 aufs. A conditioning product, as comprised above, is made in a manner similar to that described in Example II. This product, when applied to human hair, is useful as a hair conditioner.

EXAMPLE VI

A hair conditioner, according to the present invention:

| Component | Weight % |
|---|---|
| stearoxy dimethicone | 1.00 |
| dimethicone oil (12,500 cs) | 1.00 |
| Silwet L-7002[1] | 1.00 |
| cetearyl alcohol | 3.00 |
| distearyl dimethyl ammonium chloride[2] | 2.00 |
| hydroxy ethyl cellulose | 0.50 |
| Peptein 2000[3] | 0.50 |
| Panthenol | 0.50 |
| fragrance | 0.50 |
| titanium dioxide | 0.10 |
| phosphoric acid | 0.05 |
| preservative | 0.05 |
| colorant | 0.05 |
| distilled water | 89.75 |

[1]dimethicone copolyol, sold by Union Carbide Corporation
[2]purified; absorbance in 260 nm–280 nm range of less than 0.25 aufs.
[3]hydrolyzed animal protein, sold by Geo. A. Hormel & Co.
[4]pantothenyl alcohol, provitamin of the B-complex vitamin pantothenic acid, sold by Hoffman-LaRoche, Inc.

A hair conditioning product is made in a manner similar to that described in Example II, except for processing of the cyclomethicone/dimethicone gum materials. These silicone agents are premixed under heat and agitation to form a gum solution. The gum solution is added to the conditioning product batch mix after the batch solution is cooled to approximately 48° C. The final product, when applied to human hair, is useful as a conditioning agent.

In the above example ditallow dimethyl ammonium chloride, dicetyl dimethyl ammonium chloride and ditallow dipropyl ammonium phosphate are substituted, respectively, for the distearyl dimethyl ammonium chloride, with substantially similar results.

EXAMPLE VII

A shampoo, according to the present invention:

| Component | Weight % |
|---|---|
| ammonium lauryl sulfate | 8.00 |
| ammonium laureth sulfate | 8.00 |
| polydimethyl siloxane | 3.00 |
| xanthan gum | 0.75 |
| coconut monoethanolamide | 1.00 |
| di(hydrogenated tallow) dimethyl ammonium chloride[1] | 3.50 |
| ethylene glycol distearate | 1.00 |
| ceteayl alcohol | 1.00 |
| sodium chloride | 0.57 |
| ammonium xylene sulfonate | 1.50 |
| perfume/dye solution | 1.70 |
| sodium citrate | 1.00 |
| water | q.s. 100% |

[1]purified; absorbance in 260 nm–280 nm range of less than 0.25 aufs.

What is claimed is:

1. A process for purifying an impure quaternary cationic surfactant material intended for cosmetic use and rendering said quaternary cationic surfactant materials free flowing and substantially free of UV absorbing impurities having a maximum absorption in the range of from about 260 nm to about 280 nm comprising the following steps:
   (a) washing said impure quaternary cationic surfactant materials with an organic solvent selected from the group consisting of acetonitrile, acetone, diethyl ether, and mixtures thereof;
   (b) applying suction to remove the filtrate; and
   (c) drying the solid;
wherein said impure quaternary cationic surfactant materials have the following general formula:

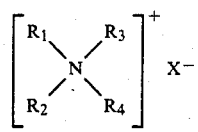

wherein $R_1$ and $R_2$ are aliphatic groups containing from about 12 to about 22 carbon atoms, $R_3$ and $R_4$ are hydrogen or short chain alkyl groups containing from about 1 to about 4 carbon atoms and X is an ion selected from halogen, acetate, phosphate, nitrate and alkyl sulfate radicals.

2. A process according to claim 1 wherein the solvent is acetonitrile.

3. A process according to claim 2 wherein at least 0.5 mls/gm acetonitrile is used.

4. A process according to claim 2 wherein at least 5 mls/gm acetonitrile is used.

5. A process for purifying an impure quaternary cationic surfactant material intended for cosmetic use and rendering the material free flowing and substantially free of UV absorbing impurities with a maximum absorption at from about 270 nm to about 275 nm comprising the following steps:
  (a) washing the impure quaternary cationic surfactant material with at least 0.5 ml/gm acetonitrile for from about 60 to about 120 minutes;
  (b) applying suction for from about 30 to about 60 minutes to remove the filtrate; and
  (c) drying the solid,
wherein said impure quaternary cationic surfactant materials have the following general formula:

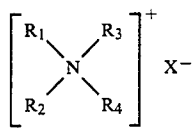

wherein $R_1$ and $R_2$ are aliphatic groups containing from about 12 to about 22 carbon atoms, $R_3$ and $R_4$ are hydrogen or short chain alkyl groups containing from about 1 to about 4 carbon atoms and X is an ion selected from halogen, acetate, phosphate, nitrate and alkyl sulfate radicals.

6. A shampoo composition comprising:
  (a) from about 0.5% to about 5% of a purified quaternary cationic surfactant material substantially free of, UV absorbing impurities with a maximum absorption at from about 270 nm to about 275 nm made by a process having the following steps:
    (i) washing the impure quaternary cationic surfactant material with at least 0.5 ml/gm acetonitrile for from about 60 to about 120 minutes;
    (ii) applying suction for from about 30 to about 60 minutes to remove the filtrate; and
    (iii) drying the solid,
  wherein said impure quaternary cationic surfactant materials have the following general formula:

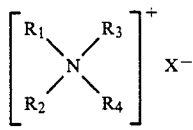

wherein $R_1$ and $R_2$ are aliphatic groups containing from about 12 to about 22 cabon atoms, $R_3$ and $R_4$ are hydrogen or short chain alkyl groups containing from about 1 to about 4 carbon atoms and X is an ion selected from halogen, acetate, phosphate, nitrate and alkyl sulfate radicals;
  (b) from about 0.5% to about 5% of a siloxane conditioning compound;
  (c) from about 5% to about 50% of a synthetic anionic surfactant;
  (d) from about 0.4% to about 3% of a suspending agent; and
  (e) water.

7. A shampoo composition according to claim 6 wherein the purified quaternary cationic surfactant material is selected from the group consisting of ditallow dimethyl ammonium chloride, distearyl dimethyl ammonium chloride, dicetyl dimethyl ammonium chloride, ditallow dimethyl ammonium phosphate, and di(-hydrogenated tallow) dimethyl ammonium chloride.

* * * * *